US007906667B2

(12) United States Patent
Sasaki

(10) Patent No.: US 7,906,667 B2
(45) Date of Patent: Mar. 15, 2011

(54) METHOD FOR PRODUCING OPTICALLY ACTIVE ALCOHOL COMPOUND

(75) Inventor: Kazuaki Sasaki, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 299 days.

(21) Appl. No.: 12/161,695

(22) PCT Filed: Jan. 31, 2007

(86) PCT No.: PCT/JP2007/052070
§ 371 (c)(1),
(2), (4) Date: Jul. 22, 2008

(87) PCT Pub. No.: WO2007/089025
PCT Pub. Date: Aug. 9, 2007

(65) Prior Publication Data
US 2010/0234629 A1 Sep. 16, 2010

(30) Foreign Application Priority Data
Feb. 1, 2006 (JP) ................................. 2006-024214

(51) Int. Cl.
*C09B 45/00* (2006.01)
*C07C 37/00* (2006.01)
(52) U.S. Cl. ............................ 556/34; 568/715; 568/771
(58) Field of Classification Search .................... 556/34; 568/715, 771; 534/34
See application file for complete search history.

(56) References Cited

U.S. PATENT DOCUMENTS

| 6,916,963 B2 | 7/2005 | Van Hal et al. |
| 6,995,110 B2 | 2/2006 | Sasaki |
| 2003/0216250 A1 | 11/2003 | Kim et al. |
| 2004/0053779 A1 | 3/2004 | Larrow et al. |

FOREIGN PATENT DOCUMENTS

| EP | 1153657 A | 11/2001 |
| JP | 60-215671 A | 10/1985 |
| JP | 5-59718 B2 | 8/1993 |
| JP | 10-330389 A | 12/1998 |
| JP | 2003-2854 A | 1/2003 |
| JP | 2004-285003 A | 10/2004 |
| JP | 2005-538838 A | 12/2005 |

OTHER PUBLICATIONS

Zhang et al., Tetrahedron Letters, vol. 46, pp. 5403-5408 (Aug. 2005).*
Lepage, Carmela R. Jackson et al., The oxidation of sulfides by chromium (V), Canadian Journal of Chemistry, (2003), 81(1), pp. 75-80.
Samsel, E.G. et al., Mechanism of the chromium-catalyzed epoxidation of olefins. Role of oxochromium (V) cations, Journal of the American Chemical Society, (1985), 107 (25), pp. 7606-7617.
J. Ready et al., "Asymmetric Catalytic Synthesis of alpha-Aryloxy Alcohols: Kinetic Resolution of Terminal Epoxides via Highly Enantioselective Ring-Opening with Phenois", J. Am. Chem. Soc., (1999), 121, pp. 6086-6087.
E. Jacobsen et al., "Electronic Tuning of Asymmetric Catalysts", J. Am. Chem. Soc., (1991), 113, pp. 6703-6704.
W. Zhang et al., "Asymmetric Olefin Epoxidation with Sodium Hypochlorite Catalyzed by Easily Prepared Chiral Mn(III) Salen Complexes", J. Org. Chem., (1991), 56, pp. 2296-2298.
Kobayashi S., "Immobilized Catalysts in Combinatorial Chemistry", Current Opinion in Chemical Biology, vol. 4, Jun. 1, 2000, pp. 338-345.
Depu Chen et al., "Lewis Acid-Catalyzed Reactions in Protic Media. Lanthanide-Catalyzed Reactions of Indoles with Aldehydes or Ketones", Tetrahedron Letters, vol. 37, No. 26, 1996, pp. 4467-4470.
Sibi M. P., et al. "Temperature Dependent Reversal of Stereochemistry in Enantioselective Conjugate Amine Additions", Tetrahedron, vol. 58, No. 41, Oct. 7, 2002, pp. 8357-8363.

* cited by examiner

*Primary Examiner* — Porfirio Nazario Gonzalez
(74) *Attorney, Agent, or Firm* — Sughrue Mion, PLLC

(57) ABSTRACT

A method for producing an optically active alcohol compound comprising reacting a cyclic ether compound with a phenol compound in the presence of an asymmetric complex obtained by reacting an optically active metal complex represented by the formula (1):

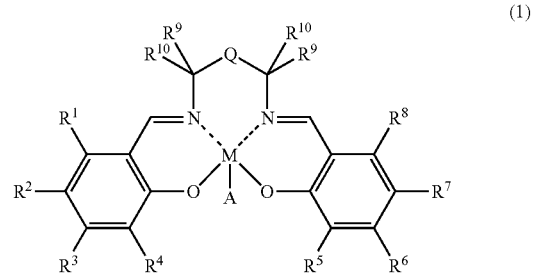

wherein $R^1$, $R^2$, $R^3$, $R^4$, $R^5$, $R^6$, $R^7$ and $R^8$ are the same or different and each independently represent a hydrogen atom, an alkyl group or the like;
one of $R^9$ and $R^{10}$ is a hydrogen group and the other is a substituted or unsubstituted phenyl group or the like;
Q represents a single bond, a C1-C4 alkylene group or the like;
M represents a metal ion; and when an ionic valency of the metal ion is same as a coordination number of a ligand, A is nonexistent, and when the above-mentioned ionic valency is different from the coordination number, and A represents a counter ion or a ligand, with a metal sulfonate.

11 Claims, No Drawings

METHOD FOR PRODUCING OPTICALLY ACTIVE ALCOHOL COMPOUND

TECHNICAL FIELD

The present invention relates to a method for producing an optically active alcohol compound.

BACKGROUND ART

An optically active alcohol compound represented by optically active 1-(4-phenoxyphenoxy)-2-propanol is useful, for example, as a synthetic intermediate of pharmaceuticals and agrichemicals (e.g. JP 60-215671 A and JP 5-59718 B). As a method for producing an optically active alcohol compound, a method comprising reacting a phenol compound with a cyclic ether compound using an optically active salen metal complex as a catalyst has been known (e.g. J. Am. Chem. Soc., 121, 6086-6087 (1999)). Alternatively, a method comprising reacting a phenol compound with a cyclic ether compound using a complex catalyst obtained by reacting an optically active salen metal complex with a Lewis acid selected from the group consisting of an aluminum halide, a dialkyl aluminum halide, a trialkoxy aluminum, a titanium halide, a tetraalkoxy titanium, a boron halide and a zinc halide has been also known (e.g. U.S. Pat. No. 6,995,110). However, since the optically active salen metal complex is expensive, industrially, a development of a catalyst showing a higher activity has been desired.

DISCLOSURE OF THE INVENTION

The present invention is to provide a method for producing an optically active alcohol compound comprising reacting a cyclic ether compound with a phenol compound in the presence of an asymmetric complex obtained by reacting an optically active metal complex represented by the formula (1):

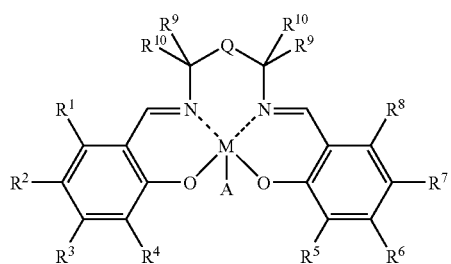

(1)

wherein $R^1$, $R^2$, $R^3$, $R^4$, $R^5$, $R^6$, $R^7$ and $R^8$ are the same or different and each independently represent a hydrogen atom, a halogen atom, an alkyl group, an alkenyl group, an alkynyl group, an alkoxy group, a haloalkyl group, a haloalkoxy group, a substituted or unsubstituted aryl group, an aralkyl group, a hydroxyl group, a nitro group, an amino group, a carbamoyl group, a carboxyl group, or a silyl group; or two adjacent groups of $R^1$, $R^2$, $R^3$, $R^4$, $R^5$, $R^6$, $R^7$ and $R^8$ are combined together to represent a naphthalene ring by forming a ring together with a benzene ring to which they are attached; one of $R^9$ and $R^{10}$ is a hydrogen group and the other is a phenyl group or a naphthyl group optionally substituted with at least one selected from the group consisting of a C1-C4 alkyl group optionally substituted with a halogen atom, a C1-C4 alkoxy group optionally substituted with a halogen atom and a halogen atom; or either one pair of $R^9$ and $R^{10}$ attached to the different carbon atoms are combined together at their ends to form a tetramethylene group and the other pair are hydrogen atoms;
Q represents a single bond or a C1-C4 alkylene group; or Q is combined with $R^9$ and $R^{10}$ to represent a 1,1'-binaphthyl group attached to the nitrogen atoms at 2 and 2' positions;
M represents a metal ion; and when an ionic valency of the metal ion is same as a coordination number of a ligand, A is nonexistent, and when the above-mentioned ionic valency is different from the coordination number, and A represents a counter ion or a ligand, with a metal sulfonate.

BEST MODE FOR CARRYING OUT THE PRESENT INVENTION

First, a novel asymmetric complex obtained by reacting an optically active metal complex represented by the above-mentioned formula (1) (hereinafter, simply referred to as the optically active metal complex (1)) with a metal sulfonate will be illustrated.

In the formula of the optically active metal complex (1), $R^1$, $R^2$, $R^3$, $R^4$, $R^5$, $R^6$, $R^7$ and $R^8$ are the same or different and each independently represent a hydrogen atom, a halogen atom, an alkyl group, an alkenyl group, an alkynyl group, an alkoxy group, a haloalkyl group, a haloalkoxy group, a substituted or unsubstituted aryl group, an aralkyl group, a hydroxyl group, a nitro group, an amino group, a carbamoyl group, a carboxyl group, or a silyl group.

Examples of the halogen atom include a fluorine atom, a chlorine atom and a bromine atom.

Examples of the alkyl group include a C1-C6 straight chain, branched chain or cyclic alkyl group such as a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, an n-hexyl group, a cyclopentyl group and a cyclohexyl group.

Examples of the alkenyl group include a C2-C6 straight chain, branched chain or cyclic alkenyl group such as a vinyl group, a propenyl group, a 1-butenyl group, a 2-butenyl group, a 2-methyl-1-propenyl group, a pentenyl group, a hexenyl group and a cyclohexenyl group.

Examples of the alkynyl group include a C2-C6 straight chain or branched chain alkynyl group such as an ethynyl group, a propynyl group, a 1-butynyl group, a 2-butynyl group and a hexynyl group.

Examples of the alkoxy group include a C1-C6 straight chain, branched chain or cyclic alkoxy group such as a methoxy group, an ethoxy group, an n-propoxy group, an isopropoxy group, an n-butoxy group, an isobutoxy group, a sec-butoxy group, a tert-butoxy group, an n-hexyloxy group and a cyclohexyloxy group.

Examples of the haloalkyl group include those obtained by substituting the above-mentioned halogen atom(s) for at least one hydrogen atom of the above-mentioned alkyl group, and specifically, a chloromethyl group, a chloroethyl group, a fluoromethyl group, a trifluoromethyl group and the like are exemplified.

Examples of the haloalkoxy group include those obtained by substituting the above-mentioned halogen atom(s) for at least one hydrogen atom of the above-mentioned alkoxy group, and specifically, a chloromethoxy group, a chloroethoxy group, a fluoroethoxy group, a trifluoromethoxy group and the like are exemplified.

Examples of the unsubstituted aryl group include a C6-C10 unsubstituted aryl group such as a phenyl group and a naphthyl group. Examples of the substituent of the substituted aryl group include the above-mentioned halogen atom, the above-mentioned alkyl group, the above-mentioned alkoxy group, a nitro group. Specific examples of the substituted aryl group include a toluoyl group, a xylyl group, a nitrophenyl group and a methoxyphenyl group.

Examples of the aralkyl group include those obtained by substituting the above-mentioned substituted or unsubstituted aryl group(s) for at least one hydrogen atom of the above-mentioned alkyl group, and specifically, a benzyl group, a triphenylmethyl group, a 1-methyl-1-phenylethyl group and the like are exemplified.

Examples of the silyl group include a silyl group substituted with three hydrocarbon groups, and examples of the hydrocarbon group include the above-mentioned alkyl group and the above-mentioned substituted or unsubstituted aryl group. Specific examples thereof include a trimethylsilyl group, a triethylsilyl group, a triphenylsilyl group and a tert-butyldimethylsilyl group.

Alternatively, two adjacent groups of $R^1$, $R^2$, $R^3$, $R^4$, $R^5$, $R^6$, $R^7$ and $R^8$ are combined together to represent a naphthalene ring by forming a ring together with a benzene ring to which they are attached.

In the above-mentioned (1), one of $R^9$ and $R^{10}$ is a hydrogen group and the other is a phenyl group or a naphthyl group optionally substituted with at least one selected from the group consisting of a C1-C4 alkyl group optionally substituted with a halogen atom, a C1-C4 alkoxy group optionally substituted with a halogen atom and a halogen atom; or either one pair of $R^9$ and $R^{10}$ attached to the different carbon atoms are combined together at their ends to form a tetramethylene group and the other pair are hydrogen atoms.

Examples of the halogen atom include a fluorine atom, a chlorine atom and a bromine atom.

Examples of the C1-C4 alkyl group include a straight chain or branched chain alkyl group such as a methyl group, an ethyl group, an n-propyl group, an isopropyl group, an n-butyl group and a tert-butyl group. Examples of the halogen atom of the C1-C4 alkyl group substituted with a halogen atom include a fluorine atom, a chlorine atom and a bromine atom. Specific examples of the C1-C4 alkyl group substituted with a halogen atom include a chloromethyl group, a chloroethyl group, a fluoroethyl group and a trifluoromethyl group.

Examples of the C1-C4 alkoxy group include a straight chain or branched chain alkoxy group such as a methoxy group, an ethoxy group, an n-propoxy group, an isopropoxy group, an n-butoxy group and a tert-butoxy group. Examples of the halogen atom of the C1-C4 alkoxy group substituted with a halogen atom include a fluorine atom, a chlorine atom and a bromine atom. Specific examples of the C1-C4 alkoxy group substituted with a halogen atom include a chloromethoxy group, a chloroethoxy group, a fluoroethoxy group and a trifluoromethoxy group.

Examples of the phenyl group or the naphthyl group optionally substituted with at least one selected from the group consisting of a C1-C4 alkyl group optionally substituted with a halogen atom, a C1-C4 alkoxy group optionally substituted with a halogen atom and a halogen atom include a phenyl group, a 1-naphthyl group, a 2-naphthyl group, a 2-methylphenyl group, a 3-methylphenyl group, a 4-methylphenyl group, a 2-methoxyphenyl group, a 3-methoxyphenyl group, a 4-methoxyphenyl group, a 2-chlorophenyl group, a 3-chlorophenyl group, a 4-chlorophenyl group, a 2-fluorophenyl group, a 3-fluorophenyl group, a 4-fluorophenyl group, a 4-bromophenyl group, a 2-trifluoromethylphenyl group, a 3-trifluoromethylphenyl group, a 4-trifluoromethylphenyl group and a 2-methyl-1-naphthyl group.

Q represents a single bond or a C1-C4 alkylene group. Alternatively, Q is combined with $R^9$ and $R^{10}$ to represent a 1,1'-binaphthyl group attached to the nitrogen atoms at 2 and 2' positions. Examples of the C1-C4 alkylene group include a methylene group, an ethylene group, a trimethylene group and a tetramethylene group.

In the above-mentioned formula (1), M represents a metal ion; and when an ionic valency of the metal ion is same as a coordination number of a ligand, A is nonexistent, and when the above-mentioned ionic valency is different from the coordination number, A represents a counter ion or a ligand.

Examples of the metal ion include a cobalt ion, a chromium ion and a manganese ion. Examples of the counter ion or the ligand include a halogen ion such as a chloride ion, a bromide ion and an iodide ion; a perfluoroalkoxide ion such as a nonafluoro-tert-butoxide ion; and an acetate ligand, and in the viewpoint of easy preparing, the halogen ion is preferable and the iodide ion is more preferable.

Examples of the optically active metal complex (1) include
(R,R)-(−)-N,N'-bis(3,5-di-tert-butylsalicylidene)-1,2-cyclo hexanediamino cobalt (III) iodide,
(R,R)-(−)-N,N'-bis(3,5-di-tert-butylsalicylidene)-1,2-cyclo hexanediamino cobalt (III) chloride,
(R,R)-(−)-N,N'-bis(3,5-di-tert-butylsalicylidene)-1,2-cyclo hexanediamino cobalt (III) bromide,
(R,R)-(−)-N,N'-bis(3,5-di-tert-butylsalicylidene)-1,2-cyclo hexanediamino cobalt (III) acetate,
(R,R)-(−)-N,N'-bis(3,5-di-tert-butylsalicylidene)-1,2-cyclo hexanediamino cobalt (III) nonafluoro-tert-butoxide,
(R,R)-(−)-N,N'-bis(3,5-di-tert-butylsalicylidene)-1,2-cyclo hexanediamino cobalt (III) hexafluoroisopropoxide,
(R,R)-(−)-N,N'-bis(salicylidene)-1,2-cyclohexanediamino cobalt (III) iodide,
(R,R)-(−)-N,N'-bis(salicylidene)-1,2-cyclohexanediamino cobalt (III) chloride,
(R,R)-(−)-N,N'-bis(salicylidene)-1,2-cyclohexanediamino cobalt (III) bromide,
(R,R)-(−)-N,N'-bis(salicylidene)-1,2-cyclohexanediamino cobalt (III) acetate,
(R,R)-(−)-N,N'-bis(salicylidene)-1,2-cyclohexanediamino cobalt (III) nonafluoro-tert-butoxide,
(R,R)-(−)-N,N'-bis(3-tert-butyl-5-methylsalicylidene)-1,2-cyclohexanediamino cobalt (III) iodide,
(R,R)-(−)-N,N'-bis(3-tert-butyl-5-methylsalicylidene)-1,2-cyclohexanediamino cobalt (III) chloride,
(R,R)-(−)-N,N'-bis(3-tert-butyl-5-methylsalicylidene)-1,2-cyclohexanediamino cobalt (III) bromide,
(R,R)-(−)-N,N'-bis(3-tert-butyl-5-methylsalicylidene)-1,2-cyclohexanediamino cobalt (III) acetate,
(R,R)-(−)-N,N'-bis(3-tert-butyl-5-methylsalicylidene)-1,2-cyclohexanediamino cobalt (III) nonafluoro-tert-butoxide,
(R,R)-(−)-N,N'-bis(3-tert-butyl-5-nitrosalicylidene)-1,2-cyclohexanediamino cobalt (III) iodide,
(R,R)-(−)-N,N'-bis(3-tert-butyl-5-nitrosalicylidene)-1,2-cyclohexanediamino cobalt (III) chloride,
(R,R)-(−)-N,N'-bis(3-tert-butyl-5-nitrosalicylidene)-1,2-cyclohexanediamino cobalt (III) bromide,
(R,R)-(−)-N,N'-bis(3-tert-butyl-5-nitrosalicylidene)-1,2-cyclohexanediamino cobalt (III) acetate,
(R,R)-(−)-N,N'-bis(3-tert-butyl-5-nitrosalicylidene)-1,2-cyclohexanediamino cobalt (III) nonafluoro-tert-butoxide,
(R,R)-(−)-N,N'-bis(3-tert-butyl-5-methoxysalicylidene)-1,2-cyclohexanediamino cobalt (III) iodide,
(R,R)-(−)-N,N'-bis(3-tert-butyl-5-methoxysalicylidene)-1,2-cyclohexanediamino cobalt (III) chloride,
(R,R)-(−)-N,N'-bis(3-tert-butyl-5-methoxysalicylidene)-1,2-cyclohexanediamino cobalt (III) bromide, (R,R)-(−)-N,N'-bis(3-tert-butyl-5-methoxysalicylidene)-1,2-cyclohexanediamino cobalt (III) acetate,
(R,R)-(−)-N,N'-bis(3-tert-butyl-5-methoxysalicylidene)-1,2-cyclohexanediamino cobalt (III) nonafluoro-tert-butoxide,
(R,R)-(−)-N,N'-bis(3-tert-butyl-5-chlorosalicylidene)-1,2-cyclohexanediamino cobalt (III) iodide,
(R,R)-(−)-N,N'-bis(3-tert-butyl-5-chlorosalicylidene)-1,2-cyclohexanediamino cobalt (III) chloride,
(R,R)-(−)-N,N'-bis(3-tert-butyl-5-chlorosalicylidene)-1,2-cyclohexanediamino cobalt (III) bromide,
(R,R)-(−)-N,N'-bis(3-tert-butyl-5-chlorosalicylidene)-1,2-cyclohexanediamino cobalt (III) acetate,
(R,R)-(−)-N,N'-bis(3-tert-butyl-5-chlorosalicylidene)-1,2-cyclohexanediamino cobalt (III) nonafluoro-tert-butoxide,
(R,R)-(−)-N,N'-bis(3-tert-butylsalicylidene)-1,2-cyclohexanediamino cobalt (III) iodide,
(R,R)-(−)-N,N'-bis(3-tert-butylsalicylidene)-1,2-cyclohexanediamino cobalt (III) chloride,
(R,R)-(−)-N,N'-bis(3-tert-butylsalicylidene)-1,2-cyclohexanediamino cobalt (III) bromide,
(R,R)-(−)-N,N'-bis(3-tert-butylsalicylidene)-1,2-cyclohexanediamino cobalt (III) acetate,
(R,R)-(−)-N,N'-bis(3-tert-butylsalicylidene)-1,2-cyclohexanediamino cobalt (III) nonafluoro-tert-butoxide,
(R,R)-(−)-N,N'-bis[(5-methyl-3-(1-methyl-1-phenylethyl)salicylidene)-1,2-cyclohexanediamino cobalt (III) iodide,
(R,R)-(−)-N,N'-bis[(5-methyl-3-(1-methyl-1-phenylethyl)salicylidene)-1,2-cyclohexanediamino cobalt (III) chloride,
(R,R)-(−)-N,N'-bis[(5-methyl-3-(1-methyl-1-phenylethyl)salicylidene)-1,2-cyclohexanediamino cobalt (III) bromide,
(R,R)-(−)-N,N'-bis[(5-methyl-3-(1-methyl-1-phenylethyl)salicylidene)-1,2-cyclohexanediamino cobalt (III) acetate,
(R,R)-(−)-N,N'-bis[(5-methyl-3-(1-methyl-1-phenylethyl)salicylidene)-1,2-cyclohexanediamino cobalt (III) nonafluoro-tert-butoxide,
(R,R)-(−)-N,N'-bis(3-tert-butyl-5-triphenylmethylsalicylidene)-1,2-cyclohexanediamino cobalt (III) iodide,
(R,R)-(−)-N,N'-bis(3-tert-butyl-5-triphenylmethylsalicylidene)-1,2-cyclohexanediamino cobalt (III) chloride,
(R,R)-(−)-N,N'-bis(3-tert-butyl-5-triphenylmethylsalicylidene)-1,2-cyclohexanediamino cobalt (III) bromide,
(R,R)-(−)-N,N'-bis(3-tert-butyl-5-triphenylmethylsalicylidene)-1,2-cyclohexanediamino cobalt (III) acetate,
(R,R)-(−)-N,N'-bis(3-tert-butyl-5-triphenylmethylsalicylidene)-1,2-cyclohexanediamino cobalt (III) nonafluoro-tert-butoxide,
(R,R)-(−)-N,N'-bis[5-tert-butyl-3-(1-methyl-1-phenylethyl)salicylidene]-1,2-cyclohexanediamino cobalt (III) iodide,
(R,R)-(−)-N,N'-bis[5-tert-butyl-3-(1-methyl-1-phenylethyl)salicylidene]-1,2-cyclohexanediamino cobalt (III) chloride,
(R,R)-(−)-N,N'-bis[5-tert-butyl-3-(1-methyl-1-phenylethyl)salicylidene]-1,2-cyclohexanediamino cobalt (III) bromide,
(R,R)-(−)-N,N'-bis[5-tert-butyl-3-(1-methyl-1-phenylethyl)salicylidene]-1,2-cyclohexanediamino cobalt (III) acetate,
(R,R)-(−)-N,N'-bis[5-tert-butyl-3-(1-methyl-1-phenylethyl)salicylidene]-1,2-cyclohexanediamino cobalt nonafluoro-tert-butoxide,
(R,R)-(−)-N,N'-bis(3,5-di-tert-butylsalicylidene)-1,2-diphenylethylenediamino cobalt (III) iodide,
(R,R)-(−)-N,N'-bis(3,5-di-tert-butylsalicylidene)-1,2-diphenylethylenediamino cobalt (III) chloride,
(R,R)-(−)-N,N'-bis(3,5-di-tert-butylsalicylidene)-1,2-diphenylethylenediamino cobalt (III) bromide,
(R,R)-(−)-N,N'-bis(3,5-di-tert-butylsalicylidene)-1,2-diphenylethylenediamino cobalt (III) acetate,
(R,R)-(−)-N,N'-bis(3,5-di-tert-butylsalicylidene)-1,2-diphenylethylenediamino cobalt (III) nonafluoro-tert-butoxide,
(R,R)-(−)-N,N'-bis(3,5-di-tert-butylsalicylidene)-1,2-diphenylethylenediamino cobalt (III) hexafluoroisopropoxide,
(R,R)-(−)-N,N'-bis(3,5-di-tert-butylsalicylidene)-1,2-cyclohexanediamino chromium (III) iodide,
(R,R)-(−)-N,N'-bis(3,5-di-tert-butylsalicylidene)-1,2-cyclohexanediamino chromium (III) chloride,
(R,R)-(−)-N,N'-bis(3,5-di-tert-butylsalicylidene)-1,2-cyclohexanediamino chromium (III) bromide,
(R,R)-(−)-N,N'-bis(3,5-di-tert-butylsalicylidene)-1,2-cyclohexanediamino chromium (III) acetate,
(R,R)-(−)-N,N'-bis(3,5-di-tert-butylsalicylidene)-1,2-cyclohexanediamino chromium (III) nonafluoro-tert-butoxide,
(R,R)-(−)-N,N'-bis(salicylidene)-1,2-cyclohexanediamino chromium (III) iodide,
(R,R)-(−)-N,N'-bis(salicylidene)-1,2-cyclohexanediamino chromium (III) chloride,
(R,R)-(−)-N,N'-bis(salicylidene)-1,2-cyclohexanediamino chromium (III) bromide,
(R,R)-(−)-N,N'-bis(salicylidene)-1,2-cyclohexanediamino chromium (III) acetate,
(R,R)-(−)-N,N'-bis(salicylidene)-1,2-cyclohexanediamino chromium (III) nonafluoro-tert-butoxide,
(R,R)-(−)-N,N'-bis(3-tert-butyl-5-methylsalicylidene)-1,2-cyclohexanediamino chromium (III) chloride,
(R,R)-(−)-N,N'-bis(3-tert-butyl-5-methylsalicylidene)-1,2-cyclohexanediamino chromium (III) bromide,
(R,R)-(−)-N,N'-bis(3-tert-butyl-5-methylsalicylidene)-1,2-cyclohexanediamino chromium (III) acetate,
(R,R)-(−)-N,N'-bis(3-tert-butyl-5-methylsalicylidene)-1,2-cyclohexanediamino chromium (III) iodide,
(R,R)-(−)-N,N'-bis(3-tert-butyl-5-nitrosalicylidene)-1,2-cyclohexanediamino chromium (III) acetate,
(R,R)-(−)-N,N'-bis(3-tert-butyl-5-nitrosalicylidene)-1,2-cyclohexanediamino chromium (III) iodide,
(R,R)-(−)-N,N'-bis(3-tert-butyl-5-nitrosalicylidene)-1,2-cyclohexanediamino chromium (III) chloride,
(R,R)-(−)-N,N'-bis(3-tert-butyl-5-nitrosalicylidene)-1,2-cyclohexanediamino chromium (III) bromide,
(R,R)-(−)-N,N'-bis(3-tert-butyl-5-methoxysalicylidene)-1,2-cyclohexanediamino chromium (III) iodide,
(R,R)-(−)-N,N'-bis(3-tert-butyl-5-methoxysalicylidene)-1,2-cyclohexanediamino chromium (III) chloride,
(R,R)-(−)-N,N'-bis(3-tert-butyl-5-methoxysalicylidene)-1,2-cyclohexanediamino chromium (III) bromide,
(R,R)-(−)-N,N'-bis(3-tert-butyl-5-methoxysalicylidene)-1,2-cyclohexanediamino chromium (III) acetate,
(R,R)-(−)-N,N'-bis(3-tert-butyl-5-chlorosalicylidene)-1,2-cyclohexanediamino chromium (III) iodide,
(R,R)-(−)-N,N'-bis(3-tert-butyl-5-chlorosalicylidene)-1,2-cyclohexanediamino chromium (III) chloride,
(R,R)-(−)-N,N'-bis(3-tert-butyl-5-chlorosalicylidene)-1,2-cyclohexanediamino chromium (III) bromide,
(R,R)-(−)-N,N'-bis(3-tert-butyl-5-chlorosalicylidene)-1,2-cyclohexanediamino chromium (III) acetate,
(R,R)-(−)-N,N'-bis(3-tert-butylsalicylidene)-1,2-cyclohexanediamino chromium (III) iodide,
(R,R)-(−)-N,N'-bis(3-tert-butylsalicylidene)-1,2-cyclohexanediamino chromium (III) chloride,
(R,R)-(−)-N,N'-bis(3-tert-butylsalicylidene)-1,2-cyclohexanediamino chromium (III) bromide, (R,R)-(−)-N,N'-bis(3-tert-butylsalicylidene)-1,2-cyclohexanediamino chromium (III) acetate,
(R,R)-(−)-N,N'-bis(3,5-di-tert-butylsalicylidene)-1,2-diphenylethylenediamino chromium (III) iodide,
(R,R)-(−)-N,N'-bis(3,5-di-tert-butylsalicylidene)-1,2-diphenylethylenediamino chromium (III) chloride,
(R,R)-(−)-N,N'-bis(3,5-di-tert-butylsalicylidene)-1,2-diphenylethylenediamino chromium (III) bromide,
(R,R)-(−)-N,N'-bis(3,5-di-tert-butylsalicylidene)-1,2-diphenylethylenediamino chromium (III) acetate,
(R,R)-(−)-N,N'-bis(3,5-di-tert-butylsalicylidene)-1,2-diphenylethylenediamino chromium (III) nonafluoro-tert-butoxide,
(R,R)-(−)-N,N'-bis(3,5-di-tert-butylsalicylidene)-1,2-cyclohexanediamino manganese (III) iodide,
(R,R)-(−)-N,N'-bis(3,5-di-tert-butylsalicylidene)-1,2-cyclohexanediamino manganese (III) chloride,
(R,R)-(−)-N,N'-bis(3,5-di-tert-butylsalicylidene)-1,2-cyclohexanediamino manganese (III) bromide,
(R,R)-(−)-N,N'-bis(3,5-di-tert-butylsalicylidene)-1,2-cyclohexanediamino manganese (III) acetate,
(R,R)-(−)-N,N'-bis(3,5-di-tert-butylsalicylidene)-1,2-cyclohexanediamino manganese (III) nonafluoro-tert-butoxide,
(R,R)-(−)-N,N'-bis(salicylidene)-1,2-cyclohexanediamino manganese (III) iodide,
(R,R)-(−)-N,N'-bis(salicylidene)-1,2-cyclohexanediamino manganese (III) chloride,
(R,R)-(−)-N,N'-bis(salicylidene)-1,2-cyclohexanediamino manganese (III) bromide,
(R,R)-(−)-N,N'-bis(salicylidene)-1,2-cyclohexanediamino manganese (III) acetate,
(R,R)-(−)-N,N'-bis(3-tert-butyl-5-nitrosalicylidene)-1,2-cyclohexanediamino manganese (III) iodide,
(R,R)-(−)-N,N'-bis(3-tert-butyl-5-nitrosalicylidene)-1,2-cyclohexanediamino manganese (III) chloride,
(R,R)-(−)-N,N'-bis(3-tert-butyl-5-nitrosalicylidene)-1,2-cyclohexanediamino manganese (III) bromide,
(R,R)-(−)-N,N'-bis(3-tert-butyl-5-methylsalicylidene)-1,2-cyclohexanediamino manganese (III) acetate,
(R,R)-(−)-N,N'-bis(3-tert-butyl-5-methylsalicylidene)-1,2-cyclohexanediamino manganese (III) nonafluoro-tert-butoxide,
(R,R)-(−)-N,N'-bis(3-tert-butyl-5-nitrosalicylidene)-1,2-cyclohexanediamino manganese (III) acetate,
(R,R)-(−)-N,N'-bis(3-tert-butyl-5-methoxysalicylidene)-1,2-cyclohexanediamino manganese (III) iodide,
(R,R)-(−)-N,N'-bis(3-tert-butyl-5-methoxysalicylidene)-1,2-cyclohexanediamino manganese (III) chloride,
(R,R)-(−)-N,N'-bis(3-tert-butyl-5-methoxysalicylidene)-1,2-cyclohexanediamino manganese (III) bromide,
(R,R)-(−)-N,N'-bis(3-tert-butyl-5-methoxysalicylidene)-1,2-cyclohexanediamino manganese (III) acetate,
(R,R)-(−)-N,N'-bis(3-tert-butyl-5-chlorosalicylidene)-1,2-cyclohexanediamino manganese (III) iodide,
(R,R)-(−)-N,N'-bis(3-tert-butyl-5-chlorosalicylidene)-1,2-cyclohexanediamino manganese (III) chloride,
(R,R)-(−)-N,N'-bis(3-tert-butyl-5-chlorosalicylidene)-1,2-cyclohexanediamino manganese (III) bromide,
(R,R)-(−)-N,N'-bis(3-tert-butyl-5-chlorosalicylidene)-1,2-cyclohexanediamino manganese (III) acetate,
(R,R)-(−)-N,N'-bis(3-tert-butylsalicylidene)-1,2-cyclohexanediamino manganese (III) iodide,
(R,R)-(−)-N,N'-bis(3-tert-butylsalicylidene)-1,2-cyclohexanediamino manganese (III) chloride,
(R,R)-(−)-N,N'-bis(3-tert-butylsalicylidene)-1,2-cyclohexanediamino manganese (III) bromide,
(R,R)-(−)-N,N'-bis(3-tert-butylsalicylidene)-1,2-cyclohexanediamino manganese (III) acetate,
(R,R)-(−)-N,N'-bis[5-methyl-3-(1-methyl-1-phenylethyl)salicylidene]-1,2-cyclohexanediamino manganese (III) iodide,
(R,R)-(−)-N,N'-bis[5-methyl-3-(1-methyl-1-phenylethyl)salicylidene]-1,2-cyclohexanediamino manganese (III) chloride,
(R,R)-(−)-N,N'-bis[5-methyl-3-(1-methyl-1-phenylethyl)salicylidene]-1,2-cyclohexanediamino manganese (III) bromide,
(R,R)-(−)-N,N'-bis[5-methyl-3-(1-methyl-1-phenylethyl)salicylidene]-1,2-cyclohexanediamino manganese (III) acetate,
(R,R)-(−)-N,N'-bis(3-tert-butyl-5-triphenylmethylsalicylidene)-1,2-cyclohexanediamino manganese (III) iodide,
(R,R)-(−)-N,N'-bis(3-tert-butyl-5-triphenylmethylsalicylidene)-1,2-cyclohexanediamino manganese (III) chloride,
(R,R)-(−)-N,N'-bis(3-tert-butyl-5-triphenylmethylsalicylidene)-1,2-cyclohexanediamino manganese (III) bromide,
(R,R)-(−)-N,N'-bis(3-tert-butyl-5-triphenylmethylsalicylidene)-1,2-cyclohexanediamino manganese (III) acetate,
(R,R)-(−)-N,N'-bis[5-tert-butyl-3-(1-methyl-1-phenylethyl)salicylidene]-1,2-cyclohexanediamino manganese (III) iodide,
(R,R)-(−)-N,N'-bis[5-tert-butyl-3-(1-methyl-1-phenylethyl)salicylidene]-1,2-cyclohexanediamino manganese (III) chloride,
(R,R)-(−)-N,N'-bis[5-tert-butyl-3-(1-methyl-1-phenylethyl)salicylidene]-1,2-cyclohexanediamino manganese (III) bromide,
(R,R)-(−)-N,N'-bis[5-tert-butyl-3-(1-methyl-1-phenylethyl)salicylidene]-1,2-cyclohexanediamino manganese (III) acetate,
(R,R)-(−)-N,N'-bis(3,5-di-tert-butylsalicylidene)-1,2-diphenylethylenediamino manganese (III) iodide,
(R,R)-(−)-N,N'-bis(3,5-di-tert-butylsalicylidene)-1,2-diphenylethylenediamino manganese (III) chloride,
(R,R)-(−)-N,N'-bis(3,5-di-tert-butylsalicylidene)-1,2-diphenylethylenediamino manganese (III) bromide,
(R,R)-(−)-N,N'-bis(3,5-di-tert-butylsalicylidene)-1,2-diphenylethylenediamino manganese (III) acetate,
(R,R)-(−)-N,N'-bis(3,5-di-tert-butylsalicylidene)-1,2-diphenylethylenediamino manganese (III) nonafluoro-tert-butoxide, and optically active metal complexes in which the above configuration (R,R)-(−) is changed to (S,S)-(+).

A commercially available optically active metal complex (1) may be used and one produced according to known methods described in J. Am. Chem. Soc., 121, 6086-6087 (1999), J. Am. Chem. Soc., 113, 6703-6704 (1991), J. Org. Chem., 56, 2296-2298 (1991) or the like may be used.

The metal sulfonate is composed of a metal cation and a perfluoroalkanesulfonate anion. The metal cation is not limited so far as it is a divalent or trivalent metal cation. While, for example, a copper cation, a stannaum cation, an aluminum cation, an indium cation and the like can be used, a cation of at least one metal element selected from the group consisting of an element of Group 2 of the periodic table, an element of Group 3 of the periodic table and a lanthanoid is preferably used.

Examples of the element of Group 2 of the periodic table include magnesium, calcium and barium. Examples of the element of Group 3 of the periodic table include scandium and yttrium. Examples of the lanthanoid include lanthanum, cerium, samarium, gadolinium and ytterbium. Among them, magnesium, scandium, yttrium, lanthanum, samarium or ytterbium is preferable.

As the sulfonate anion include, a C1-C10 alkanesulfonate anion which may be substituted with a fluorine atom is usually used. Among them, a C1-C10 perfluoroalkanesulfonate anion is preferable. Examples of the C1-C10 perfluoroalkanesulfonate anion include a trifluoromethanesulfonate anion, a pentafluoroethanesulfonate anion, a heptafluoropropanesulfonate anion, a nonafluorobutanesulfonate anion and a heptadecafluorooctanesulfonate anion. In the viewpoint of availability, the trifluoromethanesulfonate anion is preferable.

Examples of the metal sulfonate include magnesium trifluoromethanesulfonate, scandium trifluoromethanesulfonate, yttrium trifluoromethanesulfonate, lanthanum trifluoromethanesulfonate, samarium trifluoromethanesulfonate, gadolinium trifluoromethanesulfonate, ytterbium trifluoromethanesulfonate, ytterbium nonafluorobutanesulfonate and ytterbium heptadecafluorooctanesulfonate.

A commercially available metal sulfonate may be used and one produced according to known methods, for example, a method comprising reacting a metal oxide with the corresponding sulfonic acid compound, or the like may be used.

The metal sulfonate may be used as it is and as a solution of an organic solvent. A metal sulfonate which is not stable to air or moisture is preferably used as a solution of an organic solvent. Examples of the organic solvent include an aliphatic hydrocarbon solvent such as hexane and heptane; and an ether solvent such as diethyl ether and tert-butyl methyl ether.

While the used amount of the metal sulfonate is not particularly limited, it is usually 0.2 to 10 moles, and preferably 0.5 to 5 moles per 1 mole of the optically active metal complex (1).

The reaction of the optically active metal complex (1) with the metal sulfonate is usually conducted in an organic solvent by contacting and mixing both of them. When the optically active metal complex (1) and the metal sulfonate are contacted and mixed, the reaction will occur to form a novel asymmetric complex.

The temperature of the reaction of the optically active metal complex (1) with the metal sulfonate is usually −50 to a reflux temperature of the reaction mixture, and preferably −25 to 50° C.

Examples of the organic solvent include an ether solvent such as diethyl ether and tert-butyl methyl ether; an aromatic hydrocarbon solvent such as toluene; a halogenated hydrocarbon solvent such as chlorobenzene and chloroform; and an aliphatic hydrocarbon solvent such as hexane. The used amount thereof is not particularly limited.

When a metal sulfonate which is not stable to moisture is used, if water is present in the reaction system, the metal sulfonate is easily decomposed; therefore, the reagents used, solvents used and the like may preferably be subjected to dehydration in advance or dehydrating agents such as molecular sieves may preferably be allowed to coexist in the reaction system.

When the optically active metal complex (1) is reacted with the metal sulfonate in an organic solvent, the solution containing a novel asymmetric complex produced is obtained, and the obtained solution may be used as it is for the following the reaction of a cyclic ether compound with a phenol compound, or the novel asymmetric complex may be isolated by, for example, concentration of the obtained solution to use for the following the reaction of a cyclic ether compound with a phenol compound.

Next, a method for producing an optically active alcohol compound comprising reacting a cyclic ether compound with a phenol compound in the presence of the novel asymmetric complex obtained by reacting the optically active metal complex (1) with the metal sulfonate described above will be illustrated.

The cyclic ether compound may be any reactive cyclic ether compound which causes ring-opening reaction by the reaction with the phenol compound, and examples thereof include a cyclic ether compound represented by the formula (2):

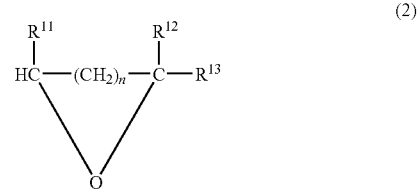

wherein $R^{11}$ represents a hydrogen atom and $R^{12}$ represents a hydrogen atom or a C1-C4 alkyl group optionally substituted; or $R^{11}$ and $R^{12}$ are combined together to represent a C2-C6 alkylene group; $R^{13}$ represents a C1-C4 alkyl group optionally substituted, a C6-C10 aryl group optionally substituted or a C7-C20 aralkyl group optionally substituted; and n represents 0 or 1.

Examples of the C1-C4 alkyl group include a straight chain or branched chain alkyl group such as a methyl group, an ethyl group, an n-propyl group, an isopropyl group, an n-butyl group and an isobutyl group. Examples of the substituent which may be substituted on these alkyl groups include a halogen atom such as a fluorine atom, a chlorine atom, a bromine atom and an iodine atom; a C1-C4 alkoxy group such as a methoxy group, an ethoxy group, an n-propoxy group, an isopropoxy group, an n-butoxy group, an isobutoxy group, a sec-butoxy group and tert-butoxy group; and a hydroxyl group. Specific examples of the alkyl group substituted with these substituents include a fluoromethyl group, a trifluoromethyl group, a methoxymethyl group and a hydroxymethyl group.

Examples of the C2-C6 alkylene group formed by combining $R^{11}$ and $R^{12}$ together include an ethylene group, a trimethylene group, a tetramethylene group, a pentamethylene group and a hexamethylene group.

Examples of the aryl group include an aryl group such as a phenyl group and a naphthyl group. Examples of the substituent which may be substituted on these aryl groups include a halogen atom such as a fluorine atom, a chlorine atom, a bromine atom and an iodine atom; a C1-C4 alkyl group such as a methyl group, an ethyl group, an n-propyl group, an isopropyl group, an n-butyl group and an isobutyl group; and a C1-C4 alkoxy group such as a methoxy group, an ethoxy group, an n-propoxy group, an isopropoxy group, an n-butoxy group, an isobutoxy group, a sec-butoxy group and tert-butoxy group. Specific examples of the aryl group substituted with these substituents include a toluoyl group, a xylyl group and a methoxyphenyl group.

Examples of the C7-C20 aralkyl group optionally substituted include those obtained by substituting the above-mentioned aryl group(s) optionally substituted for at least one hydrogen atom of the above-mentioned alkyl group optionally substituted, and specifically, a benzyl group, a triphenylmethyl group, a 1-methyl-1-phenylethyl group and the like are exemplified.

Examples of the cyclic ether compound include propylene oxide, chloromethyloxirane, bromomethyloxirane, iodomethyloxirane, 1,2-epoxybutane, 1,2-epoxyhexane, 1,3-epoxyhexane, 1,2-epoxy-4-methylpentane, 1,2-epoxy-3-phenylpropane, styrene oxide, 2,3-epoxy-1-propanol, cyclohexene oxide, cyclopentene oxide and 1,2-epoxycyclooctane. The preferred cyclic ether compound may include propylene oxide and 1,2-epoxybutane.

The phenol compound is not limited so far as it is any phenol compound having a phenolic hydroxyl group or any thiophenol compound obtained by replacing the oxygen atom in the hydroxyl group of the phenol compound by a sulfur atom, and examples thereof include a phenol compound represented by the formula (3):

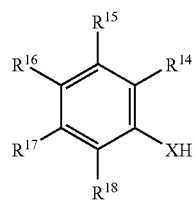

(3)

wherein X represents an oxygen atom or a sulfur atom; $R^{14}$, $R^{15}$, $R^{16}$, $R^{17}$ and $R^{18}$ are the same or different and each independently represent a hydrogen atom, a halogen atom, a nitro group, a C1-C6 alkyl group optionally substituted, a C1-C6 alkoxy group optionally substituted, or a phenoxy group optionally substituted.

Examples of the halogen atom include a fluorine atom, a chlorine atom and a bromine atom.

Examples of the C1-C6 alkyl group include a straight chain or branched chain alkyl group such as a methyl group, an ethyl group, an n-propyl group, an isopropyl group, an n-butyl group, an isobutyl group, an n-pentyl group and an n-hexyl group. Examples of the substituent which may be substituted on these alkyl groups include a halogen atom such as a fluorine atom, a chlorine atom and a bromine atom; a C1-C6 alkoxy group such as a methoxy group, an ethoxy group, an n-propoxy group, an isopropoxy group, an n-butoxy group, an isobutoxy group, a sec-butoxy group and tert-butoxy group. Specific examples of the alkyl group substituted with these substituents include a chloromethyl group, a trifluoromethyl group and a methoxymethyl group.

Examples of the C1-C6 alkoxy group include a straight chain or branched chain alkoxy group such as a methoxy group, an ethoxy group, an n-propoxy group, an isopropoxy group, an n-butoxy group, an isobutoxy group, an n-pentyloxy group and an n-hexyloxy group. Examples of the substituent which may be substituted on these alkoxy groups include a halogen atom such as a fluorine atom, a chlorine atom and a bromine atom; a C1-C6 alkoxy group such as a methoxy group, an ethoxy group, an n-propoxy group, an isopropoxy group, an n-butoxy group, an isobutoxy group, a sec-butoxy group and a tert-butoxy group. Specific examples of the alkoxy group substituted with these substituents include a chloromethoxy group, a trifluoromethoxy group and a methoxymethoxy group.

Examples of the substituent which may be substituted on the phenoxy group include a halogen atom such as a fluorine atom, a chlorine atom and a bromine atom; a C1-C6 alkyl group such as a methyl group, an ethyl group, an n-propyl group, an isopropyl group, an n-butyl group, an isobutyl group, an n-pentyl group and an n-hexyl group; and a C1-C6 alkoxy group such as a methoxy group, an ethoxy group, an n-propoxy group, an isopropoxy group, an n-butoxy group, an isobutoxy group, a sec-butoxy group and tert-butoxy group. Specific examples of the phenoxy group substituted with these substituents include a 4-chlorophenoxy group, 2-bromophenoxy group, 2-methylphenoxy group, 3-methylphenoxy group, 4-methylphenoxy group, 4-ethylphenoxy group, 4-propylphenoxy group, 2-methoxyphenoxy group, 3-methoxyphenoxy group, 4-methoxyphenoxy group, 4-ethoxyphenoxy group and 4-phenoxyphenoxy group.

Examples of the phenol compound include phenol, 4-chlorophenol, 2-bromophenol, 4-bromophenol, o-cresol, m-cresol, p-cresol, 2-methoxyphenol, 3-methoxyphenol, 4-methoxyphenol, 4-phenoxyphenol, 4-nitrophenol, 2,3-difluoro-6-nitrophenol, thiophenol, 2-bromo-4-methylthiophenol, 4-chlorothiophenol, 4-methoxythiophenol and 4-phenoxythiophenol. The preferred Examples of the phenol compound include phenol, 2-methoxyphenol, 3-methoxyphenol, 4-methoxyphenol, 4-phenoxyphenol, 4-methoxythiophenol and 4-phenoxythiophenol.

The used amount of the cyclic ether compound is usually 2 moles or more per 1 mole of the phenol compound. While there is no particular upper limit thereof, since too large amounts may easily result in an economical disadvantage, the amount thereof is practically 10 moles or less.

The reaction temperature is usually −50 to a reflux temperature of the reaction mixture, and preferably −25 to 50° C.

The reaction is conducted by contacting or mixing the asymmetric complex, the cyclic ether compound and the phenol compound. The order of mixing is not particularly limited.

The used amount of the asymmetric complex is usually 0.1 mol % or more per 1 mole of the phenol compound. While there is no particular upper limit thereof, since too large amounts may easily result in an economical disadvantage, the practical amount thereof is 0.1 to 10 mol % and preferably 0.1 to 5 mol %.

The reaction is usually carried out in the presence of an organic solvent. Examples of the organic solvent include single or mixed solvents selected from an aliphatic hydrocarbon solvent such as hexane and heptane; an aromatic hydrocarbon solvent such as toluene; an ether solvent such as diethyl ether and tert-butyl methyl ether; and a halogenated hydrocarbon solvent such as chloroform and chlorobenzene. The amounts for their use are not particularly limited.

After completion of the reaction, for example, the desired optically active alcohol compound can be isolated by concentrating the reaction mixture. Alternatively, the optically active alcohol compound can be also isolated by adding water and as necessary, a water-insoluble organic solvent to the reaction mixture to extract followed by concentrating the obtained organic layer. The isolated optically active alcohol compound may be further purified, for example, by a conventional purification means such as distillation, recrystallization and column chromatography. Examples of the water-insoluble organic solvent include an aromatic hydrocarbon solvent such as toluene and xylene; an aliphatic hydrocarbon solvent such as hexane and heptane; a halogenated hydrocarbon solvent such as chloroform and chlorobenzene; and an ether solvent such as diethyl ether and tert-butyl methyl ether. The used amount thereof is not particularly limited.

When the cyclic ether compound represented by the formula (2) and the phenol compound represented by the formula (3) are used as a cyclic ether compound and a phenol compound respectively, an optically active alcohol compound represented by the formula (4):

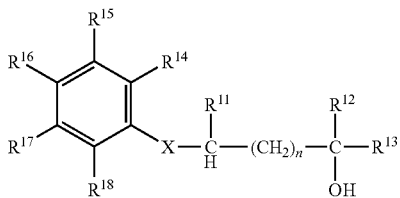

(4)

wherein $R^{11}, R^{12}, R^{13}, R^{14}, R^{15}, R^{16}, R^{17}, R^{18}$, X and n are the same as defined above is obtained.

Examples of thus obtained optically active alcohol compound include optically active 1-phenoxy-2-propanol, optically active 1-(4-chlorophenoxy)-2-propanol, optically active 1-(2-bromophenoxy)-2-propanol, optically active optically active 1-(3-methylphenoxy)-2-propanol, optically active 1-(4-methylphenoxy)-2-propanol, optically active 1-(2-methoxyphenoxy)-2-propanol, optically active 1-(3-methoxyphenoxy)-2-propanol, optically active 1-(4-methoxyphenoxy)-2-propanol, optically active 1-(4-phenoxyphenoxy)-2-propanol, optically active 1-(4-nitrophenoxy)-2-propanol, optically active 1-(2,3-difluoro-6-nitrophenoxy)-2-propanol, optically active 1-phenylthio-2-propanol, optically active 1-(2-bromo-4-methylphenylthio)-2-propanol, optically active 1-(4-chlorophenylthio)-2-propanol, optically active 1-(4-methoxyphenylthio)-2-propanol, optically active 1-(4-phenoxyphenylthio)-2-propanol, optically active 1-phenoxy-2-butanol, optically active 1-(4-chlorophenoxy)-2-butanol, optically active 1-(2-bromophenoxy)-2-butanol, optically active 1-(4-bromophenoxy)-2-butanol, optically active 1-(2-methylphenoxy)-2-butanol, optically active 1-(3-methylphenoxy)-2-butanol, optically active 1-(4-methylphenoxy)-2-butanol, optically active 1-(4-methoxyphenoxy)-2-butanol, optically active 1-(4-phenoxyphenoxy)-2-butanol, optically active 1-(4-nitrophenoxy)-2-butanol, optically active 1-(2,3-difluoro-6-nitrophenoxy)-2-butanol, optically active 1-phenylthio-2-butanol, optically active 1-(2-bromo-4-methylphenylthio)-2-butanol, optically active 1-(4-chlorophenylthio)-2-butanol, optically active 1-(4-methoxyphenylthio)-2-butanol, optically active 1-(4-phenoxyphenylthio)-2-butanol, optically active 1-phenoxy-2-hexanol, optically active 1-(4-chlorophenoxy)-2-hexanol, optically active 1-(2-bromophenoxy)-2-hexanol, optically active 1-(4-bromophenoxy)-2-hexanol, optically active 1-(2-methylphenoxy)-2-hexanol, optically active 1-(3-methylphenoxy)-2-hexanol, optically active 1-(4-methylphenoxy)-2-hexanol, optically active 1-(4-methoxyphenoxy)-2-hexanol, optically active 1-(4-phenoxyphenoxy)-2-hexanol, optically active 1-(4-nitrophenoxy)-2-hexanol, optically active 1-(2,3-difluoro-6-nitrophenoxy)-2-hexanol, optically active 1-phenylthio-2-hexanol, optically active 1-(2-bromo-4-methylphenylthio)-2-hexanol, optically active 1-(4-chlorophenylthio)-2-hexanol, optically active 1-(4-methoxyphenylthio)-2-hexanol, optically active 1-(4-phenoxyphenylthio)-2-hexanol, optically active 2-phenoxy-1-phenylethanol, optically active 2-(4-chlorophenoxy)-1-phenylethanol, optically active 2-(2-bromophenoxy)-1-phenylethanol, optically active 2-(4-bromophenoxy)-1-phenylethanol, optically active 2-(2-methylphenoxy)-1-phenylethanol, optically active 2-(3-methylphenoxy)-1-phenylethanol, optically active 2-(4-methylphenoxy)-1-phenylethanol, optically active 2-(4-methoxyphenoxy)-1-phenylethanol, optically active 2-(4-phenoxyphenoxy)-1-phenylethanol, optically active 2-(4-nitrophenoxy)-1-phenylethanol, optically active 2-(2,3-difluoro-6-nitrophenoxy)-1-phenylethanol, optically active 2-phenylthio-1-phenylethanol, optically active 2-(2-bromo-4-methylphenylthio)-1-phenylethanol, optically active 2-(4-chlorophenylthio)-1-phenylethanol, optically active 2-(4-methoxyphenylthio)-1-phenylethanol, optically active 2-(4-phenoxyphenylthio)-1-phenylethanol, optically active 1-chloro-3-phenoxy-2-propanol, optically active 1-chloro-3-(4-chlorophenoxy)-2-propanol, optically active 1-chloro-3-(2-bromophenoxy)-2-propanol, optically active 1-chloro-3-(4-bromophenoxy)-2-propanol, optically active 1-chloro-3-(2-methylphenoxy)-2-propanol, optically active 1-chloro-3-(3-methylphenoxy)-2-propanol, optically active 1-chloro-3-(4-methylphenoxy)-2-propanol, optically active 1-chloro-3-(2-methoxyphenoxy)-1-chloro-2-propanol, optically active 1-chloro-3-(3-methoxyphenoxy)-1-chloro-2-propanol, optically active 1-chloro-3-(4-methoxyphenoxy)-1-chloro-2-propanol, optically active 1-chloro-3-(4-phenoxyphenoxy)-2-propanol, optically active 1-chloro-3-(4-nitrophenoxy)-2-propanol, optically active 1-chloro-3-(2,3-difluoro-6-nitrophenoxy)-2-propanol, optically active 1-chloro-3-phenylthio-2-propanol, optically active 1-chloro-3-(2-bromo-4-methylphenylthio)-2-propanol, optically active 1-chloro-3-(4-chlorophenylthio)-2-propanol, optically active 1-chloro-3-(4-methoxyphenylthio)-2-propanol, optically active 1-chloro-3-(4-phenoxyphenylthio)-2-propanol, optically active 1-bromo-3-phenoxy-2-propanol, optically active 1-bromo-3-(4-chlorophenoxy)-2-propanol, optically active 1-bromo-3-(2-bromophenoxy)-2-propanol, optically active 1-bromo-3-(4-bromophenoxy)-2-propanol, optically active 1-bromo-3-(2-methylphenoxy)-2-propanol, optically active 1-bromo-3-(3-methylphenoxy)-2-propanol, optically active 1-bromo-3-(4-methylphenoxy)-2-propanol, optically active 1-bromo-3-(2-methoxyphenoxy)-2-propanol, optically active 1-bromo-3-(3-methoxyphenoxy)-2-propanol, optically active 1-bromo-3-(4-methoxyphenoxy)-2-propanol, optically active 1-bromo-3-(4-phenoxyphenoxy)-2-propanol, optically active 1-bromo-3-(4-nitrophenoxy)-2-propanol, optically active 1-bromo-3-(2,3-difluoro-6-nitrophenoxy)-2-propanol, optically active 1-bromo-3-phenylthio-2-propanol, optically active 1-bromo-3-(2-bromo-4-methylphenylthio)-2-propanol, optically active 1-bromo-3-(4-chlorophenylthio)-2-propanol, optically active 1-bromo-3-(4-methoxyphenylthio)-2-propanol, optically active 1-bromo-3-(4-phenoxyphenylthio)-2-propanol, optically active 3-phenoxypropane-1,2-diol, optically active 3-(4-chlorophenoxy)propane-1,2-diol, optically active 3-(2-bromophenoxy)propane-1,2-diol, optically active 3-(4-bromophenoxy)propane-1,2-diol, optically active 3-(2-methylphenoxy)propane-1,2-diol, optically active 3-(3-methylphenoxy)propane-1,2-diol, optically active 3-(4-methylphenoxy)propane-1,2-diol, optically active 3-(4-methoxyphenoxy)propane-1,2-diol, optically active 3-(4-phenoxyphenoxy)propane-1,2-diol, optically active 3-(4-nitrophenoxy)propane-1,2-diol, optically active 3-(2,3-difluoro-6-nitrophenoxy)propane-1,2-diol, optically active 3-phenylthiopropane-1,2-diol, optically active 3-(2-bromo-4-methylphenylthio)propane-1,2-diol, optically active 3-(4-chlorophenylthio)propane-1,2-diol, optically active 3-(4-methoxyphenylthio)propane-1,2-diol, optically active 3-(4-phenoxyphenylthio)propane-1,2-diol, optically active 2-phenoxycyclohexanol, optically active 2-(4-chlorophenoxy)cyclohexanol, optically active 2-(2-bromophenoxy)cyclohexanol, optically active 2-(4-bromophenoxy)cyclohexanol, optically active 2-(2-methylphenoxy)cyclohexanol, optically active 2-(3-methylphenoxy)cyclohexanol, optically active 2-(4-methylphenoxy)cyclohexanol, optically active 2-(4-methoxyphenoxy)cyclohexanol, optically active 2-(4-phenoxyphenoxy)cyclohexanol, optically active 2-(4-nitrophenoxy)cyclohexanol, optically active 2-(2,3-difluoro-6-nitrophenoxy)cyclohexanol, optically active 2-(phenylthio)cyclohexanol, optically active 2-(2-bromo-4-methylphenylthio)cyclohexanol, optically active 2-(4-chlorophenylthio)cyclohexanol, optically active 2-(4-methoxyphenylthio)cyclohexanol, optically active 2-(4-phenoxyphenylthio)cyclohexanol, optically active 2-phenoxycyclopentanol, optically active 2-(4-chlorophenoxy)cyclopentanol, optically active 2-(2-bromophenoxy)cyclopentanol, optically active 2-(4-bromophenoxy)cyclopentanol, optically active 2-(2-methylphenoxy)cyclopentanol, optically active 2-(3-methylphenoxy)cyclopentanol, optically active 2-(4-methylphenoxy)cyclopentanol, optically active 2-(4-methoxyphenoxy)cyclopentanol, optically active 2-(4-phenoxyphenoxy)cyclopentanol, optically active 2-(4-nitrophenoxy)cyclopentanol, optically active 2-(2,3-difluoro-6-nitrophenoxy)cyclopentanol, optically active 2-(phenylthio)cyclopentanol, optically active 2-(2-bromo-4-methylphenylthio)cyclopentanol, optically active 2-(4-chlorophenylthio)cyclopentanol, optically active 2-(4-methoxyphenylthio)cyclopentanol, optically active 2-(4-phenoxyphenylthio)cyclopentanol, optically active 2-phenoxycyclooctanol, optically active 2-(4-chlorophenoxy)cyclooctanol, optically active 2-(2-bromophenoxy)cyclooctanol, optically active 2-(4-bromophenoxy)cyclooctanol, optically active 2-(2-methylphenoxy)cyclooctanol, optically active 2-(3-methylphenoxy)cyclooctanol, optically active 2-(4-methylphenoxy)cyclooctanol, optically active 2-(4-methoxyphenoxy)cyclooctanol, optically active 2-(4-phenoxyphenoxy)cyclooctanol, optically active 2-(4-nitrophenoxy)cyclooctanol, optically active 2-(2,3-difluoro-6-nitrophenoxy)cyclooctanol, optically active 2-(phenylthio)cyclooctanol, optically active 2-(2-bromo-4-methylphenylthio)cyclooctanol, optically active 2-(4-chlorophenylthio)cyclooctanol, optically active 2-(4-methoxyphenylthio)cyclooctanol, and optically active 2-(4-phenoxyphenylthio)cyclooctanol.

EXAMPLES

The present invention will be illustrated in more detail by Examples below. The present invention is not limited to these Examples. Meanwhile, the yields were calculated from the results of analysis by high performance liquid chromatography. The optical purities were calculated from the results of analysis by high performance liquid chromatography using optically active columns (CHIRALCEL OD: available from DAICEL CHEMICAL INDUSTRIES, LTD.).

Example 1

Into a nitrogen-purged flask, 150.9 mg of (R,R)-(−)-N,N'-bis(3,5-di-tert-butylsalicylidene)-1,2-cyclo hexanediamino cobalt (II) and 9.5 mL of tert-butyl methyl ether were charged, and 0.5 mL of 0.25M iodine/tert-butyl methyl ether solution was further added thereto and the resultant mixture was stirred at room temperature for 30 minutes to obtain a mixture containing (R,R)-(−)-N,N'-bis(3,5-di-tert-butylsalicylidene)-1,2-cyclo hexanediamino cobalt (III) iodide. To the obtained mixture, 134 mg of yttrium trifluoromethanesulfonate was added, and the mixture was stirred for 30 minutes to prepare a catalyst solution. The catalyst solution was cooled to 5° C. and 4.71 g of phenol and 6.39 g of propylene oxide were added thereto. The mixture was stirred at the same temperature for 20 hours to achieve the reaction. After completion of the reaction, the reaction mixture was concentrated to obtain an oily matter containing 1-phenoxy-2-propanol.

Yield: 95% (based on phenol), optical purity: 96.7% e.e. (S-form)

Example 2

An oily matter containing 1-phenoxy-2-propanol was obtained according to the same as that described in Example 1, except that 149 mg of samarium trifluoromethanesulfonate was used in place of 134 mg of yttrium trifluoromethanesulfonate.

Yield: 90% (based on phenol), optical purity: 96.4% e.e. (S-form)

Example 3

An oily matter containing 1-phenoxy-2-propanol was obtained according to the same as that described in Example 1, except that 155 mg of ytterbium trifluoromethanesulfonate was used in place of 134 mg of yttrium trifluoromethanesulfonate.

Yield: 86% (based on phenol), optical purity: 96.4% e.e. (S-form)

Example 4

An oily matter containing 1-phenoxy-2-propanol was obtained according to the same as that described in Example 1, except that 123 mg of scandium trifluoromethanesulfonate was used in place of 134 mg of yttrium trifluoromethanesulfonate.

Yield: 85% (based on phenol), optical purity: 95.9% e.e. (S-form)

Example 5

An oily matter containing 1-phenoxy-2-propanol was obtained according to the same as that described in Example 1, except that 147 mg of lanthanum trifluoromethanesulfonate was used in place of 134 mg of yttrium trifluoromethanesulfonate.

Yield: 84% (based on phenol), optical purity: 96.5% e.e. (S-form)

Comparative Example 1

Into a nitrogen-purged flask, 150.9 mg of (R,R)-(−)-N,N'-bis(3,5-di-tert-butylsalicylidene)-1,2-cyclo hexanediamino cobalt (II) and 9.25 mL of tert-butyl methyl ether were charged, and 0.5 mL of 0.25M iodine/tert-butyl methyl ether solution was further added thereto and the resultant mixture was stirred at room temperature for 30 minutes to obtain a mixture containing (R,R)-(−)-N,N'-bis(3,5-di-tert-butylsalicylidene)-1,2-cyclo hexanediamino cobalt (III) iodide. To the obtained mixture, 0.25 mL of 1.0M tetraisopropoxy titanium/tert-butyl methyl ether solution was added, and the mixture was stirred for 30 minutes to prepare a catalyst solution. The catalyst solution was cooled to 5° C. and 4.71 g of phenol and 8.71 g of propylene oxide were added thereto. The mixture was stirred at the same temperature for 20 hours to achieve the reaction. After completion of the reaction, the reaction mixture was concentrated to obtain an oily matter containing 1-phenoxy-2-propanol.

Yield: 82% (based on phenol), optical purity: 97.2% e.e. (S-form)

Example 6

Into a nitrogen-purged flask, 301.9 mg of (R,R)-(−)-N,N'-bis(3,5-di-tert-butylsalicylidene)-1,2-cyclo hexanediamino cobalt (II) and 9.0 mL of tert-butyl methyl ether were charged, and 1.0 mL of 0.25M iodine/tert-butyl methyl ether solution was further added thereto and the resultant mixture was stirred at room temperature for 30 minutes to obtain a mixture containing (R,R)-(−)-N,N'-bis(3,5-di-tert-butylsalicylidene)-1,2-cyclo hexanediamino cobalt (III) iodide. To the obtained mixture, 161 mg of magnesium trifluoromethanesulfonate was added, and the mixture was stirred for 30 minutes to prepare a catalyst solution. The catalyst solution was cooled to 5° C. and 4.71 g of phenol and 6.39 g of propylene oxide were added thereto. The mixture was stirred at the same temperature for 20 hours to achieve the reaction. After completion of the reaction, the reaction mixture was concentrated to obtain an oily matter containing 1-phenoxy-2-propanol.

Yield: 88% (based on phenol), optical purity: 96.9% e.e. (S-form)

Example 7

Into a nitrogen-purged flask, 301.9 mg of (R,R)-(−)-N,N'-bis(3,5-di-tert-butylsalicylidene)-1,2-cyclo hexanediamino cobalt (II) and 3.0 mL of tert-butyl methyl ether were charged, and 1.0 mL of 0.25M iodine/tert-butyl methyl ether solution was further added thereto and the resultant mixture was stirred at room temperature for 30 minutes to obtain a mixture containing (R,R)-(−)-N,N'-bis(3,5-di-tert-butylsalicylidene)-1,2-cyclo hexanediamino cobalt (III) iodide. To the obtained mixture, 268 mg of yttrium trifluoromethanesulfonate was added, and the mixture was stirred for 30 minutes to prepare a catalyst solution. The catalyst solution was cooled to 5° C. and 1.24 g of 2-methoxyphenol and 2.78 g of 2-chloromethyloxirane were added thereto. The mixture was stirred at the same temperature for 20 hours to achieve the reaction. After completion of the reaction, the reaction mixture was concentrated to obtain an oily matter containing 1-chloro-3-(2-methoxyphenoxy)-2-propanol.

Yield: 59% (based on 2-methoxyphenol), optical purity: 84.2% e.e. (S-form)

Example 8

An oily matter containing 1-chloro-3-(2-methoxyphenoxy)-2-propanol was obtained according to the same as that described in Example 7, except that 310 mg of ytterbium trifluoromethanesulfonate was used in place of 268 mg of yttrium trifluoromethanesulfonate.

Yield: 71% (based on 2-methoxyphenol), optical purity: 87.3% e.e. (S-form)

Example 9

Into a nitrogen-purged flask, 301.9 mg of (R,R)-(−)-N,N'-bis(3,5-di-tert-butylsalicylidene)-1,2-cyclo hexanediamino cobalt (II) and 4.0 mL of tert-butyl methyl ether were charged, and 1.0 mL of 0.25M iodine/tert-butyl methyl ether solution was further added thereto and the resultant mixture was stirred at room temperature for 30 minutes to obtain a mixture containing (R,R)-(−)-N,N'-bis(3,5-di-tert-butylsalicylidene)-1,2-cyclo hexanediamino cobalt (III) iodide. To the obtained mixture, 268 mg of yttrium trifluoromethanesulfonate was added, and the mixture was stirred for 30 minutes to prepare a catalyst solution. The catalyst solution was cooled to 5° C. and 3.10 g of 2-methoxyphenol and 6.94 g of 2-chloromethyloxirane were added thereto. The mixture was stirred at the same temperature for 94 hours to achieve the reaction. After completion of the reaction, the reaction mixture was concentrated to obtain an matter containing 1-chloro-3-(2-methoxyphenoxy)-2-propanol.

Yield: 82% (based on 2-methoxyphenol), optical purity: 85.2% e.e. (S-form)

Comparative Example 2

An oily matter containing 1-chloro-3-(2-methoxyphenoxy)-2-propanol was obtained according to the same as that described in Example 7, except that 1.0 mL of 1.0M tetraisopropoxy titanium/tert-butyl methyl ether solution was used in place of 268 mg of yttrium trifluoromethanesulfonate.

Yield: 37% (based on 2-methoxyphenol), optical purity: 65.3% e.e. (S-form)

Example 10

An oily matter containing optically active 1-(4-phenoxyphenoxy)-2-propanol can be obtained according to the same as that described in Example 1, except that 4-phenoxyphenol is used in place of phenol.

Example 7

An oily matter containing optically active 1-(4-phenoxyphenoxy)-2-propanol can be obtained according to the same as that described in Example 6, except that 4-phenoxyphenol is used in place of phenol.

INDUSTRIAL APPLICABILITY

The asymmetric complex of the present invention exhibits high catalytic activity in the reaction of acyclic ether compound with a phenol compound; therefore, it is possible to produce an optically active alcohol compound more advantageous industrially by using the asymmetric complex.

The invention claimed is:
1. A method for producing an optically active alcohol compound comprising reacting a cyclic ether compound with a phenol compound in the presence of an asymmetric complex obtained by reacting an optically active metal complex represented by the formula (1):

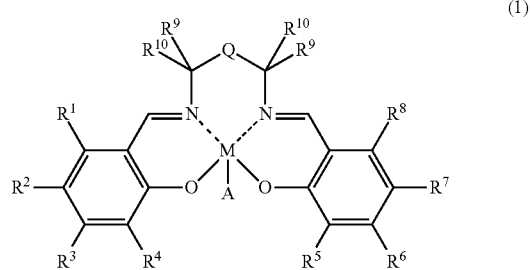

wherein $R^1$, $R^2$, $R^3$, $R^4$, $R^5$, $R^6$, $R^7$ and $R^8$ are the same or different and each independently represent a hydrogen atom, a halogen atom, an alkyl group, an alkenyl group, an alkynyl group, an alkoxy group, a haloalkyl group, a haloalkoxy group, a substituted or unsubstituted aryl group, an aralkyl group, a hydroxyl group, a nitro group, an amino group, a carbamoyl group, a carboxyl group, or a silyl group; or two adjacent groups of $R^1$, $R^2$, $R^3$, $R^4$, $R^5$, $R^6$, $R^7$ and $R^8$ are combined together to represent a naphthalene ring by forming a ring together with a benzene ring to which they are attached;

one of $R^9$ and $R^{10}$ is a hydrogen group and the other is a phenyl group or a naphthyl group optionally substituted with at least one selected from the group consisting of a C1-C4 alkyl group optionally substituted with a halogen atom, a C1-C4 alkoxy group optionally substituted with a halogen atom and a halogen atom; or either one pair of $R^9$ and $R^{10}$ attached to the different carbon atoms are combined together at their ends to form a tetramethylene group and the other pair are hydrogen atoms;

Q represents a single bond or a C1-C4 alkylene group; or Q is combined with $R^9$ and $R^{10}$ to represent a 1,1'-binaphthyl group attached to the nitrogen atoms at 2 and 2' positions;

M represents a metal ion; and when an ionic valency of the metal ion is same as a coordination number of a ligand, A is nonexistent, and when the above-mentioned ionic valency is different from the coordination number, and A represents a counter ion or a ligand, with a metal sulfonate.

2. The method according to claim 1, wherein the cyclic ether compound is a cyclic ether compound represented by the formula (2):

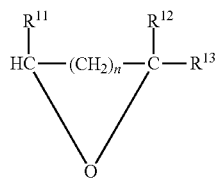

(2)

wherein $R^{11}$ represents a hydrogen atom and $R^{12}$ represents a hydrogen atom or a C1-C4 alkyl group optionally substituted; or $R^{11}$ and $R^{12}$ are combined together to represent a C2-C6 alkylene group; $R^{13}$ represents a C1-C4 alkyl group optionally substituted, a C6-C10 aryl group optionally substituted or a C7-C20 aralkyl group optionally substituted; and n represents 0 or 1;

the phenol compound is a phenol compound represented by the formula (3):

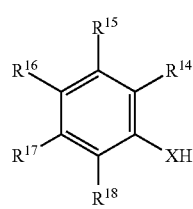

(3)

wherein X represents an oxygen atom or a sulfur atom; $R^{14}$, $R^{15}$, $R^{16}$, $R^{17}$ and $R^{18}$ are the same or different and each independently represent a hydrogen atom, a halogen atom, a nitro group, a C1-C6 alkyl group optionally substituted, a C1-C6 alkoxy group optionally substituted, or a phenoxy group optionally substituted; and the optically active alcohol compound is an optically active alcohol compound represented by the formula (4):

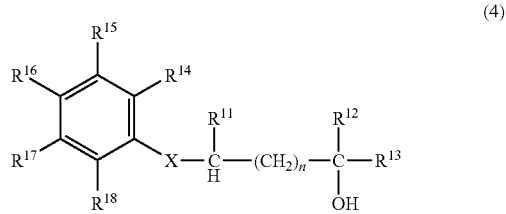

(4)

wherein $R^{11}$, $R^{12}$, $R^{13}$, $R^{14}$, $R^{15}$, $R^{16}$, $R^{17}$, $R^{18}$, X and n are the same as defined above.

3. The method according to claim 1 or 2, wherein the metal sulfonate is a metal sulfonate composed of a metal cation and a C1-C10 perfluoroalkanesulfonate anion.

4. The method according to claim 3, wherein the C1-C10 perfluoroalkanesulfonate anion is a trifluoromethanesulfonate anion.

5. The method according to claim 3, wherein the metal cation is a cation of at least one metal element selected from the group consisting of an element of Group 2 of the periodic table, an element of Group 3 of the periodic table and a lanthanoid.

6. The method according to claim 5, wherein at least one metal element selected from the group consisting of an element of Group 2 of the periodic table, an element of Group 3 of the periodic table and a lanthanoid is at least one metal element selected from the group consisting of magnesium, scandium, yttrium, lanthanum, samarium and ytterbium.

7. The method according to claim 1 or 2, wherein M is a cobalt ion, a chromium ion or a manganese ion.

8. The method according to claim 1 or 2, wherein A is a halide ion.

9. An asymmetric complex obtained by reacting the optically active metal complex according to claim 1 with a metal sulfonate, wherein the metal sulfonate is a metal sulfonate composed of a metal cation and a C1-C10 perfluoroalkanesulfonate anion, and the metal cation is a cation of at least one metal element selected from the group consisting of an element of Group 2 of the periodic table, an element of Group 3 of the periodic table and a lanthanoid.

10. The asymmetric complex according to claim 9, wherein at least one metal element selected from the group consisting of an element of Group 2 of the periodic table, an element of Group 3 of the periodic table and a lanthanoid is at least one metal element selected from the group consisting of magnesium, scandium, yttrium, lanthanum, samarium and ytterbium.

11. The asymmetric complex according to claim 9, wherein the C1-C10 perfluoroalkanesulfonate anion is a trifluoromethanesulfonate anion.

* * * * *